(12) United States Patent
Weyl et al.

(10) Patent No.: US 6,672,132 B1
(45) Date of Patent: Jan. 6, 2004

(54) SENSING ELEMENT SEAL FOR A GAS SENSOR

(75) Inventors: Helmut Weyl, Schwieberdingen (DE); Johann Wehrmann, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/214,954

(22) PCT Filed: May 14, 1998

(86) PCT No.: PCT/DE98/01342

§ 371 (c)(1),
(2), (4) Date: Sep. 13, 1999

(87) PCT Pub. No.: WO98/52030

PCT Pub. Date: Nov. 19, 1998

(30) Foreign Application Priority Data

May 15, 1997 (DE) ......................... 197 20 332
Nov. 20, 1997 (DE) ......................... 197 51 424

(51) Int. Cl.$^7$ .................................. G01N 33/497
(52) U.S. Cl. ........................................ 73/23.31
(58) Field of Search ....................... 73/23.31, 31.06, 73/31.05; 240/153.18; 204/424, 427, 426

(56) References Cited

U.S. PATENT DOCUMENTS

| | | | |
|---|---|---|---|
| 4,214,472 A | * | 7/1980 | Maxwell et al. ............ 73/23.31 |
| 4,596,132 A | | 6/1986 | Takami et al. |
| 4,786,398 A | | 11/1988 | Wertheimer et al. |
| 5,039,972 A | * | 8/1991 | Kato et al. ................ 73/31.05 |
| 5,467,636 A | | 11/1995 | Thompson et al. |
| 5,490,412 A | * | 2/1996 | Duce et al. ................ 73/23.31 |
| 5,616,825 A | * | 4/1997 | Achey et al. ............... 73/23.31 |
| 5,739,414 A | * | 4/1998 | Paulus et al. .............. 73/23.31 |
| 5,795,454 A | * | 8/1998 | Friese et al. ................ 204/424 |
| 5,817,920 A | * | 10/1998 | Kuisell et al. ............. 73/23.31 |
| 5,886,248 A | * | 3/1999 | Paulus et al. .............. 73/23.31 |

FOREIGN PATENT DOCUMENTS

EP 0 706 046 4/1996

* cited by examiner

Primary Examiner—Harshad Patel
(74) Attorney, Agent, or Firm—Kenyon & Kenyon

(57) ABSTRACT

A sensor, in particular for determining the oxygen content in exhaust gases of internal combustion engines, is provided. The sensor includes a sensing element arranged in a housing having a reference gas space-side housing part, and a sensing element seal which hermetically separates a reference gas space from a measured gas space. Provided inside the reference gas space-side housing part is a sleeve, enclosing the sensor element on a longitudinal segment, which forms a receptacle for the sensing element seal.

17 Claims, 3 Drawing Sheets

SENSING ELEMENT SEAL FOR A GAS SENSOR

BACKGROUND INFORMATION

U.S. Pat. No. 5,467,636 describes a sensor in which a planar sensing element is secured in gas-tight fashion in a ceramic shaped element by way of a sensing element seal. The sensing element seal is a glass seal which is provided, in the form of a fusible glass seal, in a depression which surrounds the sensing element and is introduced on the exhaust gas-side ceramic shaped element, and thereby separates a reference gas space from a measured gas space.

Another sensor is described in U.S. Pat. No. 4,596,132. As described therein a sensing element is mounted directly in a reference gas space-side housing part of a metal housing by way of a sensing element seal. The sensing element seal is formed by a fusible glass seal which encloses the reference gas space-side end of the sensing element together with the contacted connector cables. The sensing element operates without a reference atmosphere.

SUMMARY OF THE INVENTION

A sensor according to the present invention achieves a secure, gas-tight, and gasoline-resistant sealing of the sensing element. The sensor is of simple construction in terms of assembly engineering, and to that extent is economical to manufacture. The installation space available on the reference gas side is used in order to arrange the sensing element seal as far away as possible from the hot exhaust gas. As a result, the various coefficients of thermal expansion of the sensing element seal and solid electrolyte material of the sensing element, and the reaction behavior of the material of the sensing element seal with the solid electrolyte material of the sensing element, have less of an effect, thus creating a sensing element seal that is crack-free and reliable, at high temperatures and in the presence of temperature cycling, over its entire utilization life.

A particularly gas-tight and gasoline-resistant sensing element seal is achieved by way of a glass seal, the glass seal being introduced into the receptacle in the form of fusible glass. A further limitation in the heat flux toward the glass seal is achieved by a thermal insulation element that is arranged between the ceramic shaped element and fusible glass seal and is made of a material with poor thermal conductivity. It has proven advantageous in this context to use a presintered steatite ring which is deformed by the application of pressure into a powder packing. One advantageous embodiment, which allows the use of a preassembled subassembly made up of ceramic formed element, sensing element, inner metal sleeve, and glass seal, moreover consists in the fact that a further presintered steatite ring, which secures the ceramic shaped element in the housing by sealing, is inserted between the ceramic shaped element and the housing.

A further advantageous embodiment with a preassembled subassembly is made possible by pre-securing the sensing element in the housing. In this context, the sensing element is secured, prior to manufacture of the sensing element seal, by way of a powder packing configured between two ceramic shaped elements. The powder seal acts simultaneously as an insulator with respect to the thermal conduction occurring during manufacture of the fusible glass seal, and as an additional primary seal. The seal arrangement made up of the sensing element seal and powder packing thus forms a dual-action seal which has an additionally favorable effect on continuous operation of the sensor. The advantage of this embodiment moreover lies in the fact that no assembly forces act on the sensing element seal which is subsequently manufactured.

A further reduction in the influence of the coefficients of thermal expansion of the solid electrolyte material of the sensing element and the fusible glass is possible by the fact that a ceramic shaped element, which surrounds the sensing element and has a coefficient of thermal expansion very closely matched to the solid electrolyte material of the sensing element, is inserted into the fusible glass.

DETAILED DESCRIPTION

Figure 1:
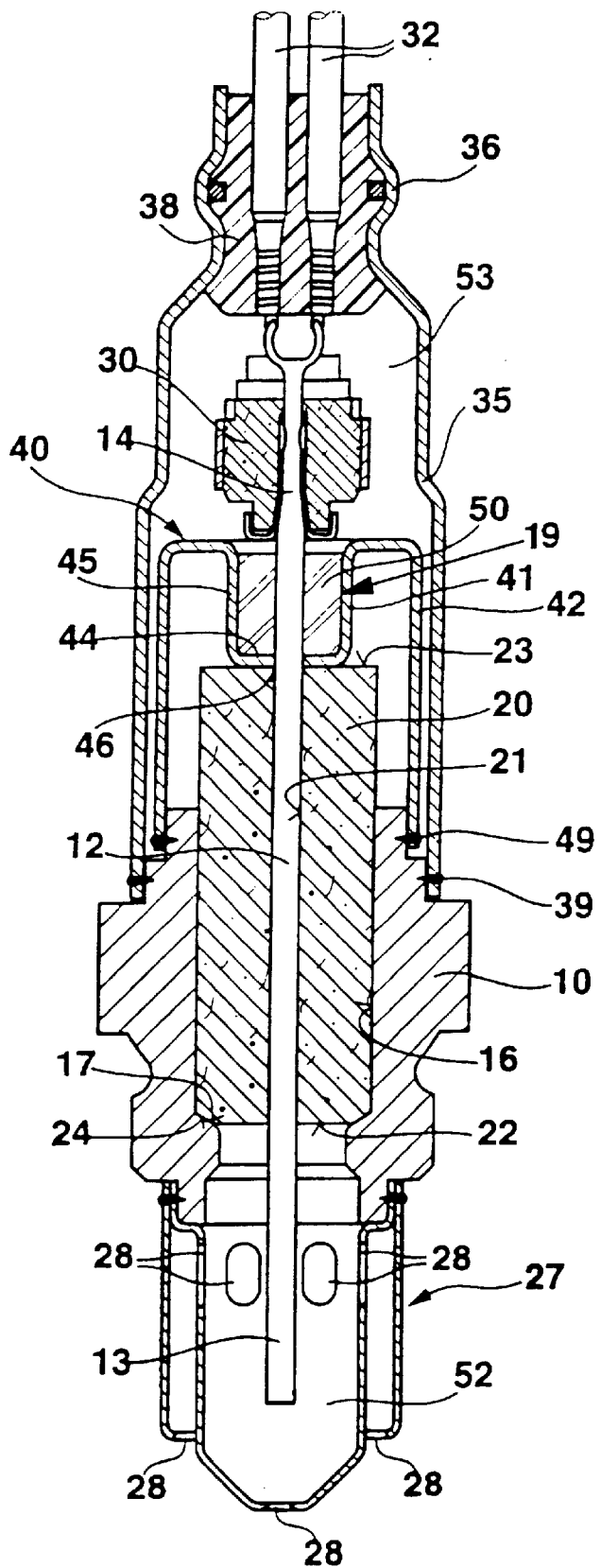
FIG. 1 shows a longitudinal section through a sensor of the present invention.

Exemplary embodiments of the present invention are depicted in the drawings and explained in more detail in the description below. FIG. 1 shows a longitudinal section through a sensor according to the present invention, FIG. 2 a portion of the sensor according to the present invention in a sectioned depiction in accordance with a second exemplary embodiment, FIG. 3 a sectioned depiction of a sensing element seal in accordance with a third exemplary embodiment, and FIG. 4 a sectioned depiction of a sensing element seal in accordance with a fourth exemplary embodiment.

The sensor depicted in FIG. 1 is an electrochemical gas sensor for determining the oxygen content in exhaust gases of internal combustion engines. The sensor has a metal housing 10 in which a flat-plate sensing element 12 with a measured gas-side end segment 13 and a reference gas space-side end segment 14 are arranged. Housing 10 is inserted via threads into an exhaust pipe (not depicted). Also configured in housing 10 is a longitudinal bore 16 having, for example, a shoulder-shaped annular surface 17.

A ceramic shaped element 20 having a passthrough 21 for sensor element 12 is arranged in longitudinal bore 16. Ceramic shaped element 20 has a measured gas-side end surface 22 and a reference gas space-side end surface 23. Measured gas-side end surface 22 is embodied, for example, with a conically profiled annular surface 24 which sits on shoulder-shaped annular surface 17. Measured gas-side end segment 13 projecting out of housing 10 extends into a measured gas space 52, and is surrounded at a distance by, for example, a double-walled protective tube 27 having gas inlet and gas outlet openings 28.

Reference gas space-side end segment 14 of sensing element 12 is surrounded by an outer metal sleeve 35 forming a reference gas space-side housing part, which has a tubular opening 36 in which a cable passthrough 38 made, for example, of PTFE is arranged. Cable passthrough 38 is caulked in gas-tight fashion to outer metal sleeve 35. Connector cables 32 are guided through cable passthrough 38. Outer metal sleeve 35 is welded in gas-tight fashion to housing 10 by way of a circumferential weld bead 39. A reference gas space 53 is constituted inside outer metal sleeve 35. Air, for example, constituting the reference atmosphere for a reference electrode (not depicted) of sensing element 12, is introduced into reference gas space 53, for example through cable passthrough 38. Sensing element 12 moreover has, on reference gas space-side end segment 14, contacts (not depicted in further detail) which make contact with connector cables 32 via a contact connector 30.

An inner metal sleeve 40 has a receptacle 41, fitting around sensing element 12, with a side wall 45 and a cylinder wall 42. In accordance with the exemplary embodiment depicted in FIG. 1, receptacle 41 is of cup-shaped configuration with a base 44. An opening 46 for the passage of sensing element 12 is present in base 44. In this exemplary embodiment, receptacle 41 is configured from the shape of inner metal sleeve 40 by way of an inward-facing indentation. This configuration makes it possible to manufacture inner metal sleeve 40 with base 44 as a one-piece deep-drawn part. Inner metal sleeve 40 is placed with base 44 of receptacle 41 onto reference gas space-side end surface 23 of ceramic shaped element 20, and welded in gas-tight fashion to housing 10 at cylinder wall 32 by way of a circumferential further weld bead 49.

Located in receptacle 41 is a sensing element seal 19 which effects a hermetic separation of reference gas space 53 from measured gas space 52. In accordance with a first exemplary embodiment depicted in FIG. 1, sensing element seal 19 comprises a glass seal 50.

A fusible glass, for example a lithium aluminum silicate glass or lithium barium aluminum silicate glass, is suitable as glass seal 50. Additives which yield an improvement in the flow behavior of the molten glass can be added to the fusible glass. In addition, powdered substances such as copper, aluminum, iron, brass, graphite, boron nitride, $MoS_2$, or a mixture of these substances can be used as additives to plasticize glass seal 50 during the joining process. Lithium carbonate, lithium soap, borax, or boric acid are used, for example, as fluxes for glass seal 50. The addition of compensating fillers, for example aluminum nitrite, silicon nitrite, zirconium tungstate, or a mixture of these substances is suitable for adjusting the thermal expansion. It is just as conceivable, however, to use another fusible material, for example a metal solder, instead of the fusible glass seal. Opening 46 in metal sleeve 40 for the passage of sensing element 12 is in this context advantageously configured with approximately zero clearance, so that no glass of glass seal 50 can penetrate through opening 46 during the melting operation.

Welding of inner metal sleeve 40 advantageously takes place by the action of a pressure onto the latter, so that ceramic shaped element 20 is pressed with annular surface 24 onto annular shoulder 17. A sealing effect does not, however, necessarily need to be established between shoulder-shaped annular surface 17 and annular surface 24. The sealing effect is implemented by weld bead 49.

Figure 2:
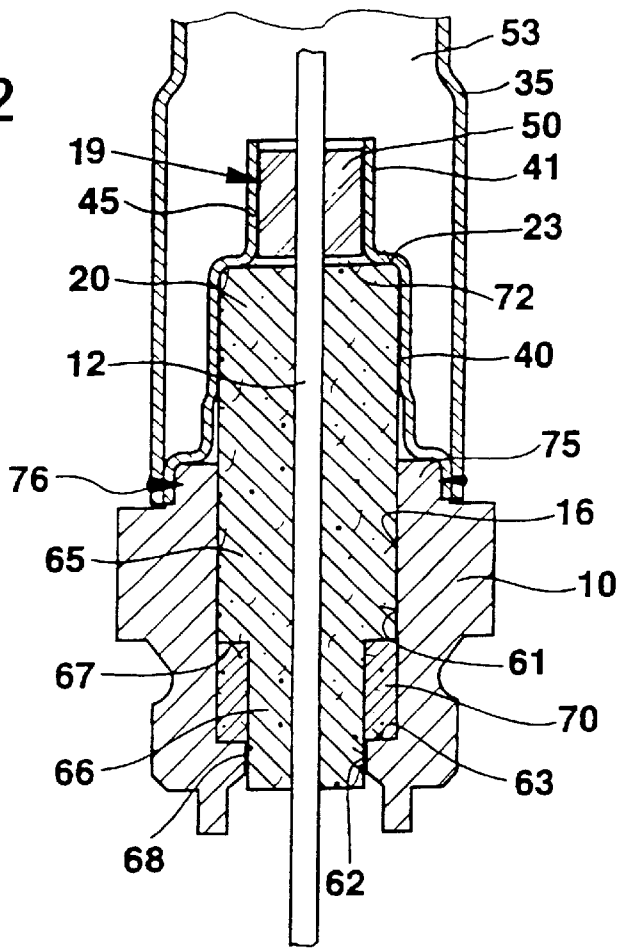
FIG. 2 is a sectioned depiction of a second embodiment of the sensor of the present invention.

A second exemplary embodiment of the sensor according to the present invention is shown in FIG. 2. In this exemplary embodiment, receptacle 41 of inner metal sleeve 40 is embodied without a base, so that reference gas space-side end surface 23 is exposed inside receptacle 41. Located in receptacle 41, on reference gas space-side end surface 23, is a thermal insulating element 72 which has poor thermal conductivity. Glass seal 50 lies above thermal insulating element 72. Thermal insulating element 72 is, for example, a powder packing that is manufactured, for example, by way of a steatite ring that is presintered at approximately 650 degrees and prior to introduction of the fusible glass seal is compressed by a compressive force so that the steatite ring deforms to powder. In this context, the powder packing serves at the same time to pre-secure sensing element 12 in ceramic shaped element 20.

In the embodiment in accordance with FIG. 2, inner metal sleeve 40 is moreover shaped in such a way that it encloses a collar 75 configured on housing 10. Outer metal sleeve 35 is slipped over this so that inner metal sleeve 40 and outer metal sleeve 35 can be welded in gas-tight fashion to housing 10 with a single weld bead 76. This embodiment requires no axial pressure on inner metal sleeve 40 during the welding operation, since ceramic shaped element 20 has previously been pressed into longitudinal bore 16 and is secured thereby. The use of a thermal insulating element 72 in the form of a powder packing is also possible with the exemplary embodiment in accordance with FIG. 1.

In the exemplary embodiment in accordance with FIG. 2, longitudinal bore 16 is moreover embodied in stepped fashion, with a large bore 61 and a small bore 62 and a planar annular surface 63 configured between bores 61 and 62. Ceramic shaped element 20 is also configured in stepped fashion, with a first cylinder 65 and a second cylinder 66 and an annular pressure surface 67 configured between cylinders 65, 66. The diameter of first cylinder 65 is adapted to the diameter of large bore 61, and the diameter of second cylinder 66 to the diameter of small bore 62, a gap 68 that is as small as possible being present between second cylinder 66 and the inner wall of small bore 62. Also located in longitudinal bore 16 is a powder seal 70, which can be manufactured in the same manner as the powder packing of thermal insulating element 72, the steatite ring necessary for the purpose being compressed between annular compression surface 67 of ceramic shaped element 20 and the planar annular surface 63 of housing 10.

A further embodiment for constituting inner metal sleeve 40 consists in the fact that receptacle 41 has a cross section adapted to the cross section of sensing element 12. In this context, an oval shape, which creates a circumferential and largely uniform small difference in spacing between sensing element 12 and side wall 45 of receptacle 41, can easily be embodied in terms of production engineering. The result is the most uniform possible stress distribution in the fusible glass of glass seal 50.

Figure 3:
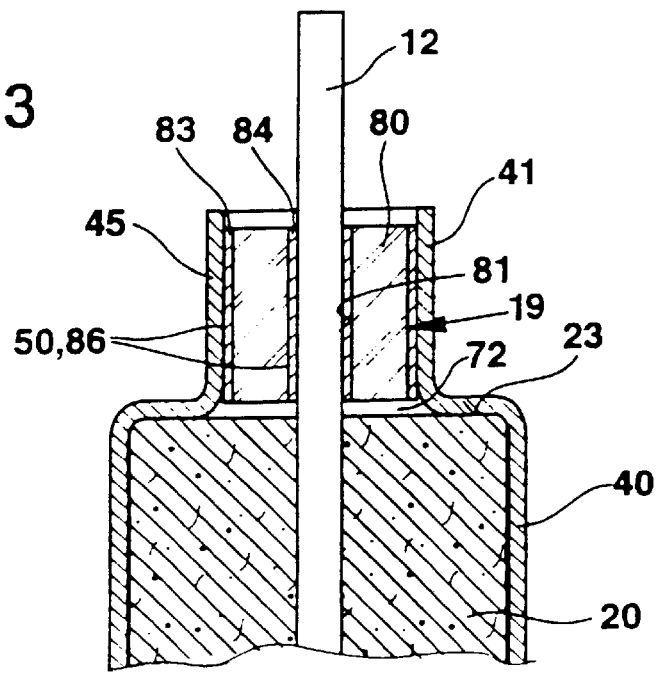
FIG. 3 is a sectioned depiction of a sensing element seal in accordance with a third embodiment of the present invention.

A further exemplary embodiment for configuring a sensing element seal is evident from FIG. 3. In this, as in the exemplary embodiment in accordance with FIG. 2, thermal insulating element 72 is arranged in receptacle 41 on reference gas space-side end surface 23 of ceramic shaped element 20. A ceramic shaped element 80 with a passthrough 81 for sensing element 12 rests on thermal insulating element 72. In this context, shaped element 80 is dimensioned so that an outer gap 83 is constituted toward side wall 45 of receptacle 41, and an inner gap 84 in passthrough 81 toward sensing element 12. A fusible glass seal 86 in the form of glass seal 50 is introduced into gaps 83, 84 so that shaped element 80 is fusibly sealed in receptacle 41. This arrangement forms sensing element seal 19. This embodiment offers the advantage that by suitable selection of the material of ceramic shaped element 80, which for example is made of $ZrO_2$, it is possible to achieve thermal expansion characteristics for sensing element seal 19 which are adapted to sensing element 12. It is thereby possible to select gap dimensions between sensing element 12 and shaped element 80 and between shaped element 80 and inner metal sleeve 40 which are favorable for an optimum seal. In addition, the fusible glass for fusible glass seal 86 can be selected with thermal expansion characteristics adapted to the sensitive sensing element 12.

Figure 4:
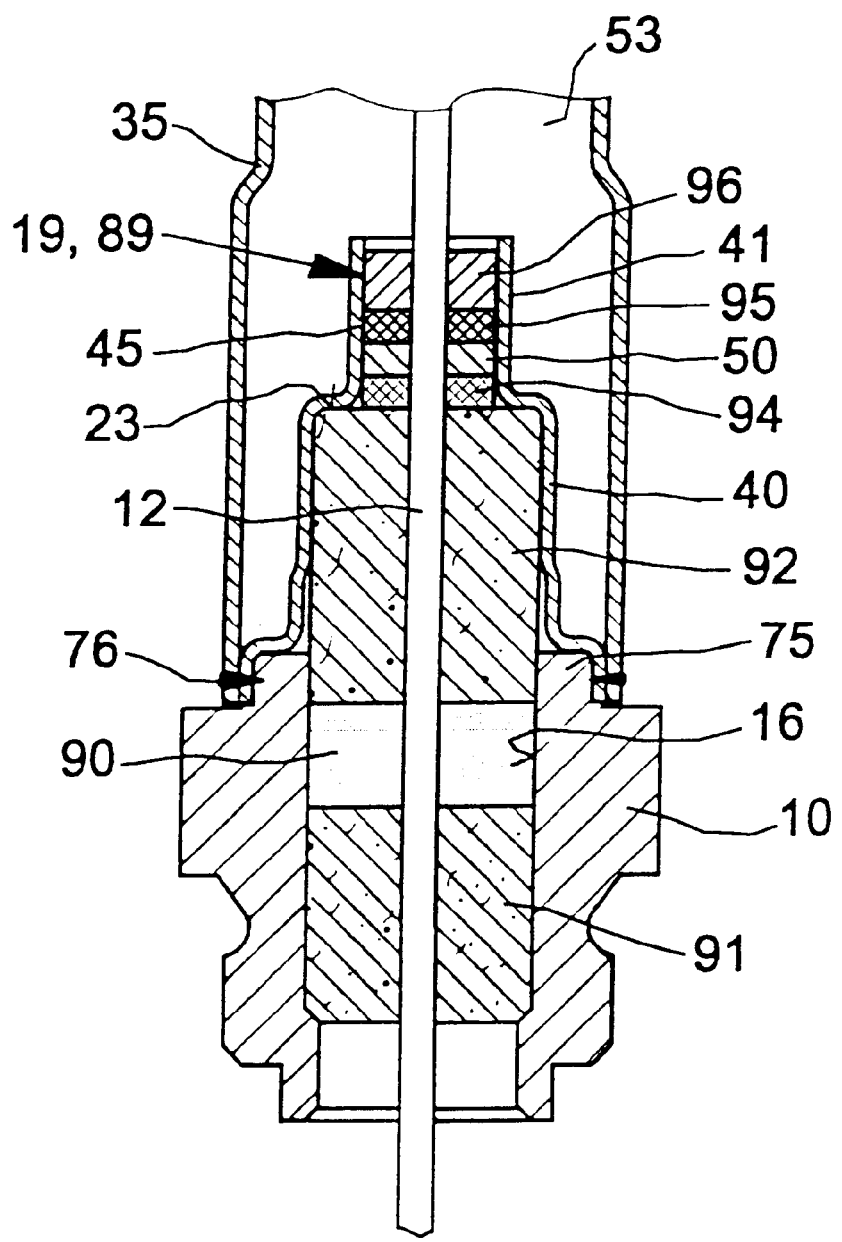
FIG. 4 is a sectioned depiction of a sensing element seal in accordance with a fourth exemplary embodiment of the present invention.

In a further exemplary embodiment depicted in FIG. 4, sensing element 12 is secured in housing 10 by way of a powder packing 90. For this purpose, a measured gas-side ceramic shaped element 91 and a reference gas space-side ceramic shaped element 92 are arranged in longitudinal bore 16 of housing 10. As in the exemplary embodiment with a single ceramic shaped element in FIG. 1, inner metal sleeve 40 is slipped over reference gas space-side ceramic shaped element 92. Inserted between the two ceramic shaped elements 91, 92 is, for example, a pre-pressed and pre-sintered steatite ring which, when inner metal sleeve 40 is pressed onto reference gas space-side ceramic shaped element 92, is deformed into powder, thus constituting powder packing 90. In the process, the steatite powder presses against sensing element 12 and longitudinal bore 16. Sensing element 12 is thereby at least pre-secured in housing 10. At the same time, powder packing 90 constitutes in housing 10 a primary seal for sensing element 12.

The exemplary embodiment in accordance with FIG. 4 shows a further embodiment of sensing element seal 19 with a seal arrangement 89. In this embodiment, a lower powder seal 94 resting on reference gas space-side ceramic shaped element 92, glass seal 50, an upper powder seal 95, and a ceramic sleeve 96 are arranged, one lying on top of another, in cup-shaped receptacle 41 of inner metal sleeve 40. As in the case of the manufacture of powder packing 90, powder seals 94, 95 are inserted, for example, as pre-pressed and pre-sintered steatite rings. In order to manufacture glass seal 50, a thermally deformable glass preform is inserted between the steatite rings. As the glass preform is heated to the softening temperature of the glass being used, a compressive force is applied onto ceramic sleeve 96. The steatite rings thereby deform into powder seals 94, 95 by analogy with the manufacture of powder packing 90. At the same time, the thermally deformable glass preform is pressed to form glass seal 50.

Pressing of seal arrangement 89 is accomplished, after sensing element 12 has been secured in housing 10, by way of powder packing 90. As a result, no assembly forces act on sensing element seal 19 when the inner and outer metal sleeves 35, 40 are later welded. It is also, however, possible to dispense with ceramic sleeve 96 acting as the pressing plunger, in which case the compressive force then acts directly on the upper steatite ring.

Seal arrangement 89 described above has the advantage that when glass seal 50 is fused or pressed, a thermal decoupling in the direction of the sensitive portion of sensing element 12 is accomplished, and a uniform pressure distribution additionally results. Sensing element 12 is thus not excessively loaded in the region of glass seal 50.

The present invention is not limited to the exemplary embodiments described. Any combinations of powder packings and powder seals with one or more glass seals are possible.

What is claimed is:

1. A sensor for determining oxygen content in exhaust gases of an internal combustion engine, comprising:
   a metal housing including a reference gas space-side housing part, the reference gas space-side housing part substantially surrounding a reference gas space;
   a measured gas-side end segment arranged with respect to a measured gas space;
   a sensing element seal positioned between the reference gas space and the measured gas space and hermetically separating the reference gas space from the measured gas space;
   a sensing element arranged in the metal housing; and
   a sleeve arranged inside the reference gas space-side housing part and enclosing the sensor element on a longitudinal sensor, the sleeve forming a receptacle for the sensing element seal.

2. The sensor according to claim 1, wherein the sleeve is joined in a gas-tight manner to the reference gas space-side housing part.

3. The sensor according to claim 1, further comprising:
   a ceramic element arranged in the metal housing, the ceramic element having an end surface facing into the reference gas space, the receptacle enclosing the end surface so that the end surface forms a base for the receptacle.

4. The sensor according to claim 1, wherein the receptacle is cup-shaped and has a base with a recess for passage of the sensing element, the sensor further comprising:
   a ceramic element arranged in the metal housing, the ceramic element having an end surface facing into the reference gas space.

5. The sensor according to claim 1, wherein the sensing element seal includes at least one glass seal.

6. The sensor according to claim 5, further comprising:
   at least one thermal insulation element arranged on below the at least one glass seal on a side of the at least one glass seal toward the measured gas space.

7. The sensor according to claim 6, wherein the at least one thermal insulation element forms a powder seal.

8. The sensor according to claim 7, wherein the glass seal is arranged between at least two powder seals.

9. The sensor according to claim 8, further comprising:
   a ceramic element arranged on the reference gas space side and resting above an outer one of the at least two powder seals.

10. The sensor according to claim 7, wherein the at least one thermal insulation element is inserted into the sensor as a pre-pressed ring, the pre-pressed ring being deformable into powder by a compressive force.

11. The sensor according to claim 5, further comprising:
    a ceramic element having a passthrough for the sensing element, the ceramic shaped element being fused into the at least one glass seal.

12. The sensor according to claim 1, wherein the sensing element is secured in the metal housing using a powder packing.

13. The sensor according to claim 12, wherein the powder packing is arranged between a first ceramic element and a second ceramic element in a pressed state.

14. The sensor according to claim 12, wherein the powder packing is formed from a pre-pressed and pre-sintered steatite ring, the steatite ring deforming into powder upon pressing.

15. The sensor according to claim 1, wherein the sensing element seal is positioned in the receptacle formed by the sleeve.

16. The sensor according to claim 15, wherein the sleeve and the receptacle together are a one-piece deep drawn part.

17. A sensor for determining oxygen content in exhaust gases of an internal combustion engine, comprising:
    a metal housing including a reference gas space-side a housing part, the reference gas space-side housing part substantially surrounding a reference gas space;
    a measured gas-side end segment arranged with respect to a measured gas space;
    a sensing element seal positioned between the reference gas space and the measured gas space and hermetically separating the reference gas space from the measured gas space;
    a sensing element arranged in the metal housing;
    a sleeve arranged inside the reference gas space-side housing part and enclosing the sensor element on a longitudinal sensor; and
    a receptacle configured to receive the sensing seal element, the sleeve and the receptacle together being a one-piece part.

* * * * *

UNITED STATES PATENT AND TRADEMARK OFFICE
CERTIFICATE OF CORRECTION

PATENT NO. : 6,672,132 B1
DATED : January 6, 2004
INVENTOR(S) : Helmut Weyl et al.

It is certified that error appears in the above-identified patent and that said Letters Patent is hereby corrected as shown below:

Column 5,
Line 63, change "sleeve forming a" to -- sleeve formed by a cup-shaped indentation to a --.

Signed and Sealed this

Second Day of November, 2004

JON W. DUDAS
*Director of the United States Patent and Trademark Office*